(12) United States Patent
Mirowski

(10) Patent No.: US 8,911,678 B2
(45) Date of Patent: Dec. 16, 2014

(54) MOISTURE AND MALODOR CONTROL SYSTEM

(71) Applicant: Elizabeth Mirowski, Riviera Beach, FL (US)

(72) Inventor: Elizabeth Mirowski, Riviera Beach, FL (US)

( * ) Notice: Subject to any disclaimer, the term of this patent is extended or adjusted under 35 U.S.C. 154(b) by 0 days.

(21) Appl. No.: 13/784,426

(22) Filed: Mar. 4, 2013

(65) Prior Publication Data

US 2013/0230431 A1    Sep. 5, 2013

Related U.S. Application Data

(60) Provisional application No. 61/606,591, filed on Mar. 5, 2012.

(51) Int. Cl.
| | | |
|---|---|---|
| A61L 9/00 | (2006.01) | |
| A61L 9/015 | (2006.01) | |
| C09K 3/00 | (2006.01) | |
| A24F 25/00 | (2006.01) | |
| A61L 9/014 | (2006.01) | |
| B01J 20/00 | (2006.01) | |

(52) U.S. Cl.
CPC . *A61L 9/014* (2013.01); *A61L 9/00* (2013.01); *B01J 20/00* (2013.01)
USPC ............. 422/306; 424/76.2; 252/380; 239/34

(58) Field of Classification Search
CPC ............... A61L 2/00; A61L 9/00; A61L 9/01; A61L 9/014
USPC .............. 422/5, 122, 306; 424/76.2; 252/380; 239/34
See application file for complete search history.

(56) References Cited

U.S. PATENT DOCUMENTS

| | | | | |
|---|---|---|---|---|
| 4,604,110 | A | * | 8/1986 | Frazier ............................ 95/128 |
| 5,732,485 | A | | 3/1998 | Laughlin |
| 2003/0024997 | A1 | * | 2/2003 | Welch et al. .................... 239/53 |
| 2003/0194416 | A1 | | 10/2003 | Shefer |
| 2004/0175404 | A1 | | 9/2004 | Shefer |

* cited by examiner

*Primary Examiner* — Monzer R Chorbaji
(74) *Attorney, Agent, or Firm* — Mountain IP

(57) ABSTRACT

Moisture and malodor control systems are disclosed. These systems provide moisture control and the sustained delivery of active volatile compounds for imparting fragrance and controlling malodor within innumerable objects and spaces, such as shoes, gloves, closets, etc. The systems utilize a novel combination of active volatiles contained within a diluent carrier and solid adsorbing compound. In some embodiments, increased release of active volatiles is triggered by the presence of moisture in the target environment. The systems of the invention may further include an accessory component for providing fragrance to the target environment and/or an accessory component for absorbing and removing malodorous compounds from the target environment.

15 Claims, No Drawings

MOISTURE AND MALODOR CONTROL SYSTEM

CROSS-REFERENCE TO RELATED APPLICATIONS

This application is based on and claims the benefit of priority of U.S. Provisional Patent Application Ser. No. 61/606,591 filed on Mar. 5, 2012, the contents of which are incorporated by reference in their entirety.

STATEMENT REGARDING FEDERALLY SPONSORED RESEARCH OR DEVELOPMENT

Not applicable.

REFERENCE TO SEQUENCE LISTING, A TABLE, OR A COMPUTER PROGRAM LISTING COMPACT DISK APPENDIX

Not applicable.

BACKGROUND OF THE INVENTION

Malodor may occur in any number of objects or interior spaces, such as shoes, clothing, closets, and car interiors. Malodor is often caused by the production of bad-smelling volatiles by bacteria, fungus, and other organisms. The production of malodorous compounds by these organisms is facilitated in moist environs, water being conducive to their growth and propagation.

Various means are known in the art for the control of malodor. For example, topical creams, powders, or sprays may be applied to surfaces. However, these approaches require that close contact be made with the target surface, and are limited in the amount of moisture that can be absorbed. They also do not allow for a variety of fragrance characteristics or perfuming since certain compounds that are necessary in the formulations have overbearing scent characteristics. Other approaches include sprays into the surrounding environment, which typically neutralize odiferous compounds in the air, but do nothing to provide sustained fragrance or odor fighting properties and cannot absorb moisture. Fragrant sachets are also employed, which provide fragrance, but not moisture control or odor removal and elimination. Another approach is the use of odor-absorbing compounds, which indiscriminately remove a broad spectrum of compounds associated with both good and bad olfactory experiences, making it almost impossible to provide or maintain pleasant fragrance characteristics in an environment. Many of these prior art methods of controlling malodor are also limited in the duration of their effect.

Accordingly, there is a need in the art for novel systems that target malodor and the moisture that encourages it. There is also a need in the art for systems that can simultaneously control malodor as well as imparting a pleasant fragrance.

SUMMARY OF THE INVENTION

Described herein is a versatile system for malodor control that facilitates moisture control and is capable of imparting pleasant fragrances. In one aspect, the invention comprises a novel system for the delivery of active volatiles to the inner spaces of a target object. The active volatiles of the invention include fragrance molecules and malodor-control compounds. Any number of fragrances may be used. The malodor-control compounds of the invention include volatiles which kill or inhibit the growth of malodor-causing organisms.

The systems of the invention are highly versatile, and may be configured for use in diverse target environments, ranging from dry to very wet, from small to large, and in areas where mild to severe malodor control is necessary. The systems of the invention are advantageously very long-lasting, and provide economical and facile moisture and malodor-control. The systems of the invention may employ any number of materials, and advantageously may be fabricated of biodegradable and environmentally friendly components.

In some embodiments, the invention employs active volatiles in combination with an adsorbing component and a diluent. The adsorbing component may comprise a desiccant, which advantageously absorbs moisture, and simultaneously releases active volatiles. Accordingly, in one aspect, the invention comprises a moisture-activated system for the release of active volatiles in the presence of moisture. Advantageously, this moisture-activated system is highly active in moist environments, where malodor-causing organisms are flourishing, and is less active when the target environment is dry, such that the active materials of the system are preserved when not required.

In some embodiments, a fragrance-emitting component is used in combination with the active volatile delivery system for sustained and long-lasting delivery of pleasant fragrances. In other embodiments, a malodor-absorbing component is utilized in combination with the active volatile delivery system, for removal of malodorous compounds from the target environment.

The inventions described herein may comprise compositions, articles of manufacture, systems, methods of using the compositions and articles of manufacture disclosed herein, and kits comprising the separate components of the systems described herein.

The inventions described herein may be used in any target environment, including but not limited to shoes, boots, sandals, ski boots, other footwear, gloves, clothing, closets, storage boxes and trunks, storage units, rooms, car interiors, etc.

The many configurations and advantages of the invention are made apparent in the comprehensive description that follows.

DETAILED DESCRIPTION OF THE INVENTION

As used herein, the term MOCS is an acronym for "Moisture and Odor Control System" and refers to embodiments of the invention which control moisture and malodor.

As used herein, the term "target environment" and "target object" will be used as follows. Target environment means the atmosphere within an area defined by the boundaries of the target object. For example, for a MOCS intended to provide odor control for a shoe, the target object for such a MOCS would be the shoe and the target environment would be the air space within the body of the shoe.

The systems of the invention comprise four basic elements: (1) an absorbing component; (2) active volatiles; (3) a diluent; and (4) an encasement. The invention may further comprise an accessory fragrance-releasing component, as well as an accessory malodor control component. Each of these elements is described in more detail below.

The Adsorbing Component

The adsorbing component is a material or mixture of materials comprising desiccants which also have an affinity for the active volatiles (which are described below). In general, it is preferred that the material used in the adsorbing component have a higher affinity for water molecules than for the compositions used at active volatiles. The adsorbing material serves two functions, (1) to sequester the active volatiles by weakly adsorbing them either alone or in a matrix of diluent, and (2) to remove water vapor from the target environment by acting as a desiccant. When water molecules are adsorbed by the adsorbing material, active volatiles and, active volatiles in a matrix of diluent are displaced and released into the target environment. Another property of the adsorbing material is that it be capable of bulk absorption of the selected liquid diluent (for example, by capillary action).

Clay desiccants may be utilized as the adsorbing component. Clay, a broad class of hydrous aluminum phyllosilicate materials, is available in numerous forms for desiccant applications. Certain forms of clay (e.g. montmorillonite) are excellent desiccants. Exemplary clay types for use in the MOCS of the invention include smectite clays, including montmorillonite and bentonite clays. Clay desiccants, such as Montmorillonite clay, are available in and may be used in many forms, including powders, granules, beads, and spheres.

Another material that may act as an adsorbing component is molecular sieve. Molecular sieves are synthetic crystalline aluminosilicates which are highly porous, and which have uniform pore sizes. Many types of molecular sieve are commercially available having variable pore sizes ranging from a few to many angstroms and having surface chemistries which are hydrophobic, hydrophilic, and other properties. For use in the invention, the molecular sieve must be sufficiently hydrophilic such that it has a high affinity for water, and should generally have a pore size adequate to adsorb volatile active compositions as well as absorb liquid diluent by capillary action. For example, molecular sieve having a pore size in excess of 8 nanometers may be utilized. Exemplary molecular sieves include zeolites, porous glass, and halloysites.

Other adsorbing materials that may be used in the practice of the invention include silica gels, mineral desiccants, calcium oxide, calcium sulfate, activated charcoal, activated alumina, and cellulose fiber.

Adsorbing materials having differing performance characteristics as a function of exposure time, ambient humidity and temperature are available. They can be used to tailor the performance characteristics of the MOCS to the properties of the selected target environment. Silica gels typically have a fast adsorbtion rates and can be used to make a faster acting MOCS. Molecular sieves can reduce relative humidity down to 10%, and they retain moisture at elevated temperatures better than other adsorbing materials. These can be used to for MOCS that are used in dry and hot environments. Calcium oxide can adsorb more water vapor at low humidities. Some adsorbing materials are of the environmental protection type, such as clay, mineral desiccants, cellulose fiber, and some types of activated charcoal and can be used to make the product environmentally friendly.

The Active Volatiles

Active volatiles make up the second component of the invention. The active volatiles comprise volatile materials which diffuse from the adsorbing component into the target environment, where they come into contact with the inner surfaces of the target object. Active volatiles are so named herein because they perform one of two functions. First, active volatiles may act as fragrances, imparting a desired scent to the target environment and the target object. Alternatively, the active volatiles may act as a malodor control agents. Some materials used as active volatiles have both a pleasant scent and are simultaneously capable of inhibiting the growth of malodor-causing organisms, and such active volatiles may function as both fragrance and malodor control agents.

In general, active volatiles that are in liquid form must be used for their facile incorporation into the MOCS of the invention.

Active volatiles comprising fragrances may be used, alone or in combination with malodor-controlling compositions. Fragrances are described in more detail below in the description of the fragrance-releasing accessory component, however it is understood that such materials may also be included in the MOCS solid when incorporated into the diluent and adsorbing component.

Malodor control agents include any substance known in the art to reduce odor, by any mode of action. Malodor control agents may comprise volatile compositions which kill or inactivate malodor-causing organisms. Malodor control agents further include compositions which neutralize malodorous volatile compounds by chemically altering them, binding them or otherwise reducing their olfactory effect.

Exemplary volatile active compositions include carvacral, thymol, methyl salicylate, caryophyllene, citral, eugenol, eugenol acetate, limonene, linalol, terpineol, cinnamic aldehyde, citronellol, citronellal, geraniol, linalyl acetate, trepanned, anthill, and sabines. Exemplary volatile active compositions further include essential oils ("botanicals") as known in the art and widely available from numerous commercial sources, including essential oils derived from Amber, Ambrette Seed, Amyris, Angelica Root, Anise/Star Anise, Arnica, Basil, Bay Laurel, Bergamot, Birch, Black Pepper, Black Spruce, Blue Tansy, Cajeput, Cacao Absolute, Cacao, Calendula, Caraway, Cardamom, Carrot, Carrot Seed, Cedar, Catnip, Chamomile, Cinnamon, Cistus, Citronella, Clary Sage, Clove, Coriander Seed, Cornmint, Copaiba Balsam, Cypress, Davana, Elemi, Eucalyptus, Everlasting (Helichrysum), Fennel, Fir Needle, Frankincense, Galbanum, Geranium, Geranium Rose, Ginger, Grapefruit, Hyssop, Inula, Jasmine, Juniper Berry, Lavender, Lemon, Lemon Myrtle, Lemon Tea Tree, Lemon Verbena, Lemongrass, Lime, Lovage, Marjoram, Mandarin, May Chang, Melissa, Myrrh, Neroli, Niaouli, Nutmeg, Orange, Oregano, Palamarosa, Palo Santo, Patchouli, Peppermint, Peru Balsam, Petitgrain, Pine Needle, Plai, Ravensara, Ravintsara, Rosalina, Rose, Rosehip, Rosemary, Rosewood, Sage, Sandalwood, Sea Buckthorn, Spearmint, Spike Lavender, Spikenard, Spruce, Tagetes, Tangerine, Tea Tree, Thyme, Tuberose, Turmeric, Valerian Root, Vanilla, Vetiver, Wintergreen, Yarrow, and Ylang Ylang.

Blends of different malodor control agents may be used. This advantageously provides a means of attacking malodor-causing organisms with compositions having multiple modes of action, preventing the evolution of resistance and resulting in more effective neutralization of such organisms. Additionally, malodor control agents of different volatilities may be used, such that a mixture of fast-evaporating and slow-evaporating compositions allows for an extended release profile.

An exemplary active volatile blend that controls malodor-causing organisms is a blend of essential oils containing tea tree oil, neroli oil, and geranium oil. For example a blend comprising 50% tea tree oil, 25% neroli oil, and 25% geranium oil may be utilized. Another exemplary blend of essential oils that can control malodor is an essential oil blend containing 1-10% clove oil, 1-10% bay laurel oil, 1-10% lemon oil, 1-10% melissa oil, 1-10% coriander oil, 1-10% eucalyptus oil, 1-10% cinnamon bark oil, 1-10% citronella oil, 1-10% palamarosa oil, and 1-10% clary sage oil. Another exemplary blend of essential oils would be a blend comprising 3% clove oil, 8% bay laurel oil, and 15% lemon oil, 10% melissa oil, 12.5% coriander oil, 18% eucalyptus oil, 3% cinnamon bark oil, 9% citronella oil, 10% palamarosa oil, and 12.5% clary sage oil may be used. Any other malodor-controlling composition known in the art, including blends comprising essential oils, may be used.

The Diluent.

The third element of the MOCS is the diluent. The diluent is any composition that is (1) capable of solvating the selected active volatiles and (2) which is not adsorbed by the selected adsorbing component, is weakly adsorbed by the selected adsorbing component, or is less strongly adsorbed than water molecules by the selected adsorbing component, and (3) which is absorbed in bulk by the selected adsorbing component, for example by capillary action, physisorption and/or chemisorption. The absorption of the diluent by the adsorbing material must be such that the diluent is sequestered by the selected adsorbing compound and at room temperature does not run or leak from the solids comprising the adsorbing component. The diluent prevents strong adsorption of the active volatiles by the adsorption component, so that when water vapor is present, water vapor can effectively displace adsorbed active volatiles from the adsorption component, resulting in moisture-activated release of the active volatiles. The diluent also functions as a carrier of the active volatiles and allows for release of active volatiles from the adsorption component in environments with little moisture. The diluent also acts to impede the re-adsorption of active volatiles from the target environment after they have been released from the MOCS.

Preferred diluents are liquid at room temperature (about 15-25 C). Materials which are solids at room temperature may be utilized, however their admixture with the active volatiles and adsorbing component requires heating during the manufacture process, which may damage the active volatiles. Materials which are solid at room temperature (for example, glycols having a molecular weight of about 1500 or greater) may be utilized, and will have a slower release rate of active volatiles than lower molecular weight materials, which may be useful for applications where an especially long effective life is desired. Such materials may utilize a higher amount of active volatiles to offset the lower rate of release.

A glycol (or blend of glycols) may serve as the diluent. Exemplary glycols include ethylene glycol, polyethylene glycol, propylene glycol, polypropylene glycol, dipropylene glycol and tripropylene glycol. For example, polypropylene glycol having a molecular weight between 76.1 and 192 g/mol may be utilized. For example, polyethylene glycol having a molecular weight between 62.07 and 194.2 g/mol may be utilized.

Polymeric glycols, for example polypropylene glycol and polyethylene glycol, are available in a range of molecular weights. Lower molecular weight compounds are more volatile than higher molecular weight glycols. Di- and tri-glycols, such as dipropylene glycol, tripropylene glycol, diethylene glycol, and triethylene glycol are generally less volatile than mono-glycols. Blends of polymeric glycols having various molecular weights, or blends of mono-, di-, and tri-forms of glycol will have variable volatility, depending on the relative proportions of the constituents.

Selecting an appropriate glycol or glycol blend for a particular application will generally depend on the amount of water vapor in the target environment. For example, if the target environment is a closet, the relative humidity will be much lower than that encountered in a scuba booty. Likewise, a MOCS utilized in an arid locale such as the desert Southwest of the United States will encounter less water vapor than a MOCS utilized in a humid locale, such as the southeast United States. Accordingly, the volatility of the diluent can be selected for optimal performance in the target environment and locale. In a dry target environment, a more volatile glycol is preferred, since there is relatively less water vapor available and the rate of displacement of adsorbed active volatiles will be reduced. Therefore, the use of a more volatile glycol will facilitate liberation of the active volatiles from the adsorbing component. Conversely, in a wet target environment, a less volatile glycol should be used to prevent large amounts of water vapor from quickly driving the active volatiles out of the adsorbing component. Guided by the exemplary embodiments set forth below, one of skill in the art will be able to readily select the proper glycol or blend of glycols for the desired application.

Formulating and Manufacturing the MOCS Solid

The MOCSs of the invention comprise a solid or semi-solid material made up of the following three components: the adsorbing component, the active volatiles, and the diluent. This material, for ease of reference, will hereafter be referred to herein as "MOCS solid." In general, the adsorbing component is a solid, such as a powder or preferably a granular material with average granular dimensions of 1-5 mm, and this material will hold the active volatiles and the diluent within.

The first step in manufacturing the MOCS solid is to solvate the active volatiles in the diluent. This may be accomplished by mixing the diluent with the active volatiles, for example, a liquid glycol and an essential oil, and then allowing the two ingredients to sit in a sealed vessel for a period of time (e.g. 24 hours) until the active volatiles is/are fully solvated by the diluent.

The next step is to infuse the adsorbing component with the diluent-active volatiles mixture. The liquid diluent (with dissolved active volatiles) is poured onto the solid comprising the adsorbing component and the two are mixed, and then allowed to sit in a sealed vessel for a period of time (e.g. 24 hours) until the liquid has been absorbed by the adsorbing component, such that the resulting material is dry to the touch.

The relative proportions of the various ingredients in the MOCS solid will be dictated by (1) the intended function of the MOCS and (2) the nature of the target environment. For example, if moisture control is a major function of the MOCS, then a larger proportion of adsorbing component will be necessary to promote effective desiccation of the target environment. If malodor control is a major function of the system, then a larger proportion of active volatiles will be necessary to effect aggressive malodor control. Likewise, if the target environment is wet (e.g. a ski boot or scuba equipment), a relatively larger proportion of adsorbing component will be necessary to prevent waterlogging of the system and the premature displacement of the active volatiles. Conversely, if the target environment is relatively dry (e.g. a closet or open footwear such as a sandal), relatively less adsorbing component will be necessary.

When preparing the mixture of active volatiles and diluent, the proportion of active volatiles may range from 5-75% volume, for example in the range of 15-40% volume. In general, a mixture of about 25% active volatiles by volume is preferred. When adding the mixture of active volatiles and diluent to the adsorbing material, the amount of adsorbing material necessary to effectively soak up the diluent-active volatile solution will vary depending on the type of adsorbing material used. For example, when using Montmorillonite clay, each gram of clay may effectively absorb about 0.3 ml of diluent-active volatile solution before becoming soft, malleable and sticky. For average target environments, the proportion of diluent-active volatile solution in the resulting solid may range from about 1-40% for example, in the range of 7-28% by weight. In wet target environments, the proportion of diluent-active volatile solution will be lower, for example in the range of 2-6%, as relatively larger amounts of adsorbing material are necessary for effective desiccant activity.

Similarly, the amount of material necessary to effect the desired outcome will depend on both the intended function of the MOCS and the nature of the target environment. A target object comprising a small volume, such as a glove or a shoe, will generally require a MOCS solid of 30-45 g; an intermediate volume, such as a duffel bag, will require a MOCS solid of 60-80 g; and a large volume, such as a closet or a room, will require a MOCS solid of 90-450 grams of material. Guided by the exemplary embodiments set forth below, one of skill in the art will be able to readily select an effective amount of ingredients, and relative proportion of ingredients for the desired application.

The Encasement

The fourth element of the MOCS is the encasement. In some embodiments, no encasement is utilized, and the MOCS solid is simply sprinkled on, or placed within, the target object. However, in general it is advantageous to utilize an encasement for neatly containing the MOCS solid, as well as combining it with accessory materials, as described below. The encasement is any vessel capable of holding the MOCS solid and which is permeable to gas exchange between such mixture and the surrounding environment. In some embodiments, the encasement comprises a porous material such as mesh, for example a plastic mesh with pore sizes of less than 0.25 mm. Fabric may be used to make the encasement, for example fabrics made of cotton, polyester, hemp, silk, burlap, nylon, polyester etc. Other sheet-like materials such as Tyvek™ or Kraft paper may be utilized. Alternatively, the encasement may be made of a relatively non-permeable material such as glass, wood, or plastic (e.g. PET, PVC, HDPE, LDPE, polypropylene, polyamide, polystyrene, polylactic acid, and Plastarch™) having holes, pores, and perforations to allow gas exchange with the surrounding environment.

The encasements of the invention may comprise sealable vessels. A sealable encasement allows the user to seal the MOCS solid from the atmosphere when it is not in use, extending the effective life of the system. For example, the encasement could comprise an impermeable body having one or more openings or regions made of a permeable material. When deployed in the target environment, the openings or permeable regions of the encasement are exposed, and when not in use, the encasement comprises a means of sealing the openings (e.g. plugs) or covering the permeable region (e.g. a flap of impermeable material).

In some embodiments, the encasement comprises an impermeable vessel having one side with permeable material, such that the MOCS can be placed on a flat surface, such as the sole of a shoe, and the MOCS solid will exclusively exchange gas with the flat surface to which it is exposed, and not the surrounding atmosphere.

The encasements of the invention may be advantageously made in any shape. For example, a MOCS intended for use in a shoe could be shaped like the sole of a foot or a shoe. For example, fabric can be cut into innumerable shapes and sewn, glued, or stapled to create a vessel of any form. Solid materials can be molded, machined, or otherwise fabricated into any shape. The encasement can further be colored, printed, or adorned with other materials (e.g. tags, ribbons, sequins, etc.) to create aesthetically pleasing shapes or branded objects.

Specially configured encasements may be constructed to improve MOCS functionality in tightly packed spaces where gas exchange is constrained, for example for target objects such as tents, clothes in boxes, drawers and sleeping bags. For example, the encasement may be configured as a long strip, the strip having a repeating string of separate compartments for the MOCS solid, any accessory fragrance-releasing components, and any accessory malodor-controlling components. to ensure adequate distribution of the functional components throughout the target object. For example "sewn-through" construction, as known in the art, may be used to create a series of separate compartments. In some embodiments, the encasement has built-in airspaces to prevent compression and loss of adequate gas exchange with the target environment, for example, the encasement could utilize baffle construction, as known in the art, employing rigid materials to ensure that a certain volume of air is enclosed within the compartments housing the MOCS solid, any accessory fragrance-releasing components, and any accessory malodor-controlling components. Channel baffle construction and box baffle construction may also be used. Channel construction incorporates long channels where the material can move back and forth to aid in contact of the materials with the air. The walls can be either sewn through or have a vertical wall to provide for more air space. Box baffle construction keeps the materials in a specific volume by the use of rigid walls, for example a square area, and can be as small as 10 mm on a side, with the maximum size being the size of the overall MOCS unit. It also utilizes a rigid sidewall to prevent compression and provide a larger volume for air.

Accessor Fragrance-Releasing Component

The MOCSs of the invention may further comprise a fragrance-releasing component. While fragrances may be included as active volatiles in the MOCS solid, it is in some cases advantageous to include them in a separate component. For example, the release of fragrance from the MOCS solid may be at a low rate which is not detectable by the user, especially when the MOCS is not exposed to significant humidity. The use of a separate fragrance-releasing component allows for the MOCS to have a pleasant scent at all times, which imparts confidence in the user that the product is working, and also provides an opportunity for scent branding.

The fragrance-releasing component comprises a volatile fragrance. Many fragrances are known in the art. Exemplary fragrances include vanilla, sandalwood, pine, juniper, cedar, peppermint, wintergreen, grapefruit, lemon, and others. Fragrancing compounds extracted from plants or chemically synthesized fragrances may be included in the fragrance blends. Fragrances used in the invention may comprise at least one selected from fragrant substances listed and described by the Flavor and Extract Manufacturers Association (FEMA; FEMA permitted substances are useable as food additives) and/or the International Fragrance Manufacturers Association (IFRA; IRFA permitted substances are available for manufacturing cosmetics). Various fragrances are also listed in the International Cosmetic ingredient Dictionary and Handbook, 11th Ed. (2006), which is hereby incorporated by reference in its entirety.

The fragrances are mixed with a fixative polymer, as known in the art, in order to cause the sustained release over time of the fragrance substances. Exemplary fixatives include polypropylene glycol, polyethylene glycol, and ethylene vinyl acetate copolymer. For example polyethylene glycol 600, 3350, 4000, or 8000 may be used as fragrance fixatives (the numbers indicating the average number of carbons per molecule). For example polypropylene glycol 400, 1000, or 2000 may be used as fragrance fixatives (the numbers indicating the average number of carbons per molecule).

Fragrances are mixed with the fixative polymer by any means known in the art. For example, the solid may be mixed with the polymer at room temperature and allowed to diffuse into the polymer for 24 hours to 1 week. To facilitate faster diffusion of the fragrance compounds into the polymer, the fragrance and polymer mixture may be heated to 100° F. for 1 hour minutes and then allowed to infuse for 3-5 hours. Alternatively, the fragrance may be heated to 115° F. and immediately mixed with the polymer and allowed to infuse for 6-10 hours.

The fragrance-fixative mixture may be intermixed with the MOCS solid, for example as intermixed granules of the two compositions. Alternatively, the fragrance-fixative mixture may be separately encased within a separate portion of the encasement. For example, the encasement may comprise a dual pouch system, each pouch being physically separated from the other by a barrier, in some cases a barrier that is impermeable to gas exchange.

Accessory Malodor Control Component

In some embodiments, the invention further comprises an accessory malodor control component. The accessory malodor control component comprises a material or blend of materials that effectively adsorb malodorous compounds.

An exemplary malodor controlling component is activated carbon. Activated carbon is a form of carbon derived from organic or petroleum sources that is has an affinity for various types of molecules, and is extremely porous, which imparts an extremely high surface area for the adsorption of chemical species. Activated carbon is available in many forms, primarily defined by pore size distribution and the surface chemistry properties. For example, activated carbon having surfaces with positive, negative, acidic, or basic chemical groups are known in the art and have the ability to bind and adsorb various species.

Exemplary activated carbon types for use in the MOCSs of the invention include oxidized activated carbon. This type of activated carbon has many types of binding sites and will adsorb a broad spectrum of molecules. This type of activated carbon is especially effective for odor control as it can remove many of the diverse volatile organic malodorous compounds produced by bacteria and fungi. Another exemplary activated carbon is chemically modified activated carbon having a charged surface which is optimal for scavenging the malodorous thioesters produced by Brevibacterium. Solcarb™ KS3 (Chemviron Carbon) is a known activated carbon that improves uptake of thioesters.

Another exemplary material for the accessory malodor control component is molecular sieve.

The accessory malodor control component may be intermixed with the MOCS solid, for example as intermixed granules of the two compositions. Generally, however, it is preferred that the accessory malodor control component be separately encased within a separate portion of the encasement in order to minimize adsorption of active volatile compositions by the accessory malodor control component. For example, the encasement may comprise a dual pouch system, each pouch being physically separated from the other by a barrier, preferably a barrier that is impermeable to gas exchange. The encasement may be configured such that there is a significant distance or physical barrier between the MOCS solid and the accessory malodor control component, in order to minimize adsorption of active volatile compositions by the accessory malodor control component.

In some embodiments, the encasement comprises three separate areas (e.g. pouches, pockets, compartments, etc.) separated by material, including gas-impermeable material. The MOCS solid, an accessory fragrance component, and the accessory malodor control component each reside in one of the three separate areas of the encasement.

The relative size of the malodor control component may vary. For example, for a target object comprising a small volume target environment, such as a shoe or glove, the malodor control component may comprise 1 g-3 g of activated carbon if light malodor adsorption is desired, and 6 g-15 g or activated carbon for heavy malodor adsorption and longer product lifespan. In general, the larger the size of the malodor control component, the more active volatiles will be required in order to compensate for adsorption of the active volatiles by the malodor control component.

Recharging the MOCS

Given the design of the MOCS, it is possible to extend the life by reinfusing the MOCS with fragrance, malodor controlling compounds or both. This can be accomplished by the following steps: (1) heating the MOCS to a sufficient temperature to drive off adsorbed moisture and malodor compounds; (2) allowing the system to cool back to room temperature; (3) applying fresh liquid diluent-active volatile mixture to the encasement (or directly upon the MOCS solid if the encasement can be opened); and (4) sealing the MOCS in an airtight vessel until the fresh diluent-active volatile mixture is adsorbed. For example, for a small MOCS utilized in footwear which utilizes clay as the adsorbing component, the MOCS can be heated to 110 degrees F. for 10 hours, allowed to cool, and then 1 ml of fresh diluent-active volatile liquid is applied to the outer surface of the encasement. The MOCS is then placed in a sealed container overnight.

EXAMPLES

Example 1

Moisture and Odor Control System for Enclosed Footwear, Gloves or Like Items

This example describes a moisture and odor control system that functions in enclosed footwear, gloves, hats, and like items of users who do not need aggressive malodor control, but would like to reduce the growth of microbes and impart pleasant odors to their footwear and similar sized articles.

To prepare the MOCS solid, diluent was first combined with the active volatiles. This MOCS utilizes propylene glycol as the diluent. Approximately 2 ml of propylene glycol was mixed with 0.75 ml of essential oil blend, the essential oil blend being a mixture of various malodor-controlling botanicals having antibacterial and antifungal activities. The propylene glycol and essential oils were mixed in a sealed vessel by vigorous shaking for about 10 minutes. The sealed vessel was then allowed to sit overnight until the essential oil blend was thoroughly dissolved within the propylene glycol diluent.

The next step in preparation of the MOCS solid was to combine the diluent-essential oil mixture with the adsorbing component. The diluent-essential oil mixture was poured into an airtight vessel containing 35 grams of Montmorillonite clay, which formed the adsorbing component in this MOCS. The clay was in granular form (DesiPak™ material (Clarient), with the granules having a size and shape roughly equivalent to grains of cracked wheat. In some cases, when stronger fragrance characteristics were desired, the MOCS solid was also infused with 1 ml of fragrance. The vessel was sealed and shaken until the granules were thoroughly coated, after which it was allowed to sit overnight until the liquid mixture was thoroughly absorbed into the clay granules. The resulting MOCS solid was granular in form and dry to the touch.

Separately, an accessory fragrance component was prepared, composed of a mixture of fixative and a blend of volatile fragrances. 30 ml of fragrance blend was mixed with 448 grams of pelletized ethyl vinyl acetate fixative at room temperature. This mixture was mixed thoroughly until all pellets were coated with the fragrance, as indicated by a wet appearance and then allowed to sit in a sealed vessel for 48 hours until the fragrance was completely absorbed into the fixative. The resulting solid had a pleasant but not overpowering aroma.

A pair of identical cotton fabric encasements was prepared by cutting and gluing cotton fabric. Each encasement had one compartment. Each encasement was about 6 cm in width, about 13 cm in length and 0.6 cm in thickness, having an approximate volume of 50 cubic cm. In some versions, the encasement was shaped like a foot, in others it was shaped like an oval, a mitten, or a fish.

The MOCS solid, described above, was divided into two roughly equal portions. The accessory fragrance component, described above, was also divided into two roughly equal portions. Into the one compartment of the first cotton fabric encasement, one portion of the MOCS solid mixture was added and one portion, 3.5 g, of the accessory fragrance component was added. Both components were then enclosed, by gluing the encasement closed. This was repeated for the second encasement, resulting in a pair of MOCS suitable for use with a pair of shoes, boots, gloves, or other paired items.

MOCS prepared as described in this Example 1 were utilized in numerous footwear and glove items and were found to have effective deodorizing and scenting activity for periods of up to 12 months.

Example 2

Moisture and Odor Control System for Open Footwear or Like Items

In this Example, a moisture and odor control system that functions in open footwear such as sandals and flip-flops is described.

In this MOCS, di-propylene glycol acts as the diluent. The active volatiles in this MOCS are malodor-controlling essential oils, consisting of a combination of 50% tea tree oil, 25% neroli oil, and 25% geranium oil. Montmorillonite clay and HumiSorb™ 4A (Sorbent Systems) calcium chloride molecular sieve act as the adsorbing component in this MOCS. The MOCS solid is made by the same preparative process described in Example 1, with 1 ml of di-propylene glycol combined with 0.6 ml of essential oil blend, and this mixture being added to 23 grams of Montmorillonite clay and 23 grams of molecular sieve.

An accessory fragrance-releasing component is prepared, by the same process described in Example 1. In this MOCS, the fixative portion consists of 20 grams of PEG 4000 polymer, mixed with 1 ml of an essential oil fragrance blend, the essential oil fragrance blend being a 1:2:1 mixture of Vetiver, Pine, and Grapefruit fragrance liquids.

As in Example 1, a pair of identical fabric encasements is prepared by cutting and sewing cotton fabric. In this MOCS, each encasement has two separate compartments, each separated by a fabric wall. Each encasement is about 6 centimeter in width, about 15-26 centimeters in length and about 0.5 centimeters in thickness. One of the two large faces of the encasement is made of a gas permeable cotton fabric. The other surfaces of the encasement are made of an impermeable laminated cotton type fabric, typically laminated with polyvinyl chloride.

The MOCS solid is divided into two roughly equal portions. The accessory fragrance-releasing component is also divided into two roughly equal portions. Into one compartment of the first fabric encasement, one portion of the MOCS solid mixture is enclosed, by sewing. Into a second compartment of the first cotton fabric encasement, one portion of the accessory fragrance-releasing component is enclosed, by sewing. The process is repeated for the second encasement, resulting in a pair of MOCS suitable for use with a pair of open footwear such as sandals, flip-flops, etc.

The MOCS is placed with the permeable face of the encasement lying on the upper sole of the footwear (i.e., where the foot rests), such that active volatiles are directed towards this surface. This system provides focused release of active volatiles on the surface of the footwear that is the most prone to malodor and moisture. The use of an impermeable encasement material on the other surfaces minimizes the loss of active volatiles and fragrances to the outside atmosphere.

Example 3

Moisture and Odor Control System for Enclosed Footwear, Gloves or Like Items

This MOCS is designed for use in enclosed footwear, gloves, hats, and like items for users requiring severe malodor and moisture control. Compared to the MOCS described in Example 1, a higher degree of malodor control is enabled in this MOCS through the use of more of active volatiles and diluent, a larger proportion of active volatiles, and the use of an accessory malodor control component.

In this MOCS, liquid polypropylene glycol (mixture of 70% propylene and 30% dipropylene) acts as the diluent. The active volatiles in this MOCS are malodor controlling essential oils, consisting of a combination of 3% clove oil, 8% bay laurel oil, and 15% lemon oil, 10% melissa oil, 12.5% coriander oil, 18% eucalyptus oil, 3% cinnamon bark oil, 9% citronella oil, 10% palamarosa oil, 12.5% clary sage oil. Montmorillonite clay acts as the adsorbing component in this MOCS. The MOCS solid is made by the same preparative process described in Example 1, with 2.5 ml of polypropylene glycol combined with 2 ml of essential oil blend, and this mixture being added to 22 grams of Montmorillonite clay.

An accessory fragrance-releasing component is prepared, by the, same process described in Example 1. In this MOCS, the fixative portion consists of 9 grams of polyvinyl acetate polymer, mixed with 0.5 ml of a fragrance blend, the e fragrance blend being a 4:2:1:1 mixture of myrcene, pinene, limonene, linalool, and geraniol fragrance liquids.

As in Example 1, a pair of identical cotton fabric encasements is prepared by cutting and sewing cotton fabric. In this MOCS, each encasement has three separate compartments, each separated by a fabric wall. Each encasement is about 6 centimeters in width, about 13 centimeters in length and 1 centimeter in thickness.

The MOCS solid is divided into two roughly equal portions. The accessory fragrance-releasing component, described above, is also divided into two roughly equal portions. Into one compartment of the first cotton fabric encasement, one portion of the MOCS solid mixture is enclosed, by sewing. Into a second compartment of the first cotton fabric encasement, one portion of the accessory fragrance-releasing component is enclosed, by gluing.

Into the third compartment of the encasement, 3 grams of activated carbon [GE Technology, bamboo, surface area of 300 $m^2$/gram] is enclosed by gluing. This activated carbon forms an accessory malodor-controlling component.

The process described above is repeated for the second encasement, resulting in a pair of MOCS capable of intensive malodor control and suitable for use with a pair of shoes, boots, gloves, or other paired items.

Example 4

Moisture and Odor Control System for Medium Sized Target Objects Such as Gym Bags, Purses, and Sleeping Bags This MOCS solid was prepared as in Example 1. Approximately 3.5 ml of propylene glycol was mixed with 1 ml of essential oil blend and 1 ml of fragrance blend, and this mixture was combined with 54 grams Montmorillonite clay to form the MOCS solid.

An accessory malodor control component was prepared as well, simply made up of 6 grams of activated carbon (GE Technology, bamboo, surface area of 300 $m^2$/gram).

A cotton fabric encasement was prepared by cutting and gluing cotton fabric. The encasement had two separate compartments, separated by fabric walls, including one large compartment (about 10 by 5 by 1 centimeters) and one small compartments (about 3.0 by 5 by 1 centimeters). Into the large compartment, the MOCS solid was enclosed, by sewing. Into the small compartment, the activated carbon accessory malodor control component was enclosed, by gluing.

MOCS as described in this Example were utilized in numerous mid-sized target objects, including gym bags, purses, and sleeping bags. These MOCS were found to impart effective moisture and malodor control and pleasant scent for over 12 months.

Example 5

Moisture and Odor Control System for Large Sized Target Objects Such as Closets, Cars, and Lockers, in Humid Climates This MOCS is intended to function in large spaces such as closets, cars, lockers, etc., in humid climates.

In this MOCS, propylene glycol mixed with grapeseed oil acted as the diluent. The active volatiles in this MOCS were malodor-controlling essential oils. Montmorillonite clay and Sorb-It™ silica acted as the adsorbing component in this MOCS. The MOCS solid was made by the same preparative process described in Example 1, with 1 ml of diluent combined with 1 ml of essential oil blend, and this mixture being added to 110 grams of Montmorillonite clay and 47 grams of silica.

An accessory malodor control component was prepared as well, simply made up of 28 grams of activated carbon (GE Technology, bamboo, surface area of 300 $m^2$/gram).

A cotton fabric encasement was prepared by cutting and sewing cotton fabric. The encasement had two separate compartments, separated by fabric walls, including one large compartment (about 16 by 10 by 1 centimeters) and one small compartment (about 3 by 10 by 1 centimeter). Into the large compartment, the MOCS solid was enclosed, by sewing. Into the small compartment, the activated carbon accessory malodor control component was enclosed, by gluing.

The resulting MOCS was utilized in numerous large-sized target objects, including cars, lockers, and closets, in Florida where humidity is high. This MOCS was found to impart effective moisture and malodor control and pleasant scent for over 12 months.

Example 6

Moisture and Odor Control System for Large Sized Target Objects Such as Closets, Cars, and Lockers in Dry Climates This MOCS is intended to function in large spaces such as closets, cars, lockers, etc., in dry climates. The MOCS utilizes the following constituents:

3.5 ml of propylene glycol is utilized at the diluent;

65 grams of clay and 92 grams of molecular sieve (TriSorb™ by Clarient) act as the adsorbing component; and 27 grams of PEG 8000 fixative type is used as the fixative.

A cotton fabric encasement was prepared by cutting and sewing cotton fabric. The encasement had three separate compartments, separated by fabric walls, including one large compartment (about 16 by 10 by 1 centimeters) and two small compartments (about 2 by 10 by 1 centimeter). Into the large compartment, the MOCS solid was enclosed, by sewing. Into the first of the two small compartments, the accessory fragrance component was enclosed, by sewing. Into the second of the two small compartments the activated carbon accessory malodor control component was enclosed, by gluing.

Because not as much moisture is available to drive the release of active volatiles from the adsorbing component, a more volatile diluent is selected than that utilized in the MOCS of Example 5. TriSorb™ type molecular sieve is utilized instead of silica since it performs better at higher temperatures, especially the temperatures present in cars exposed to sun in arid environments. PEG 8000 was chosen as the fixative so as to not melt at elevated temperatures Example 7

Moisture and Odor Control System for Wet Target Objects

This MOCS is designed for use wet target objects having a target environment with extremely high moisture, for example neoprene booties, drysuits, waders, wading boots, boats shoes, rubber boots and water-logged shoes. The fabrication process is the same as that utilized in the previous Examples, with the following constituents:

0.7 ml of tripropylene glycol serves as the diluent;

0.8 ml of essential oils serve as malodor-controlling active volatiles;

74 grams of clay acts as the adsorbing component;

0.5 ml of fragrance is used with 74 grams of clay fixative as the fragrance-releasing component; and 13 grams of Coconut Shell-based Activated Carbon, such as AquaCarb™ CX (Siemens), acts as an accessory malodor-controlling component.

As above, the MOCS solid, accessory fragrance-releasing component, and accessory malodor-controlling component are sewn into three separate compartments of a fabric encasement, in this case a cylinder with a diameter measuring about 7.5 centimeters and a height of about 15.24 centimeters. Alternatively, two smaller encasements may be used when configuring this MOCS for a paired items such as scuba booties or waterlogged boots.

This MOCS is especially suited for use in very wet target objects by the use of tripropylene glycol, a less volatile diluent. The use of a less volatile diluent prevents the adsorption of water vapor from completely displacing the active volatiles in the system. Also, compared to MOCS configured for dryer target environments, this MOCS has an excess of adsorbing component, which imparts very high desiccant capabilities to the system, such that the adsorbing component does not easily become waterlogged.

All patents, patent applications, and publications cited in this specification are herein incorporated by reference to the same extent as if each independent patent application, or publication was specifically and individually indicated to be incorporated by reference. The disclosed embodiments are presented for purposes of illustration and not limitation. While the invention has been described with reference to the described embodiments thereof, it will be appreciated by those of skill in the art that modifications can be made to the structure and elements of the invention without departing from the spirit and scope of the invention as a whole.

The invention claimed is:

1. A composition for the control of moisture and malodor, comprising
   an adsorbing component comprising smectite clay;
   a diluent; and
   one or more malodor-controlling compositions.

2. The composition of claim 1 wherein
   the adsorbing component is montmorillonite clay in granular form.

3. The composition of claim 1, wherein
   the diluent is selected from a group consisting of propylene glycol, polypropylene glycol, ethylene glycol, polyethylene glycol, di-propylene glycol, and tri-propylene glycol.

4. The composition of claim 1 wherein
   the one or more malodor-controlling compositions comprises an essential oil.

5. The composition of claim 1, wherein
   the one or more malodor-controlling compositions is selected from the group consisting of carvacral, thymol, methyl salicylate, caryophyllene, citral, eugenol, eugenol acetate, limonene, linalol, terpineol, cinnamic aldehyde, citronellol, citronellal, geraniol, linalyl acetate, terpinene, anethol, sabines, essential oil of Amber, essential oil of Ambrette Seed, essential oil of Amyris, essential oil of Angelica Root, essential oil of Anise/Star Anise, essential oil of Arnica, essential oil of Basil, essential oil of Bay Laurel, essential oil of Bergamot, essential oil of Birch, essential oil of Black Pepper, essential oil of Black Spruce, essential oil of Blue Tansy, essential oil of Cajeput, essential oil of Cacao Absolute, essential oil of Cacao, essential oil of Calendula, essential oil of Caraway, essential oil of Cardamom, essential oil of Carrot, essential oil of Carrot Seed, essential oil of Cedar, essential oil of Catnip, essential oil of Chamomile, essential oil of Cinnamon, essential oil of Cistus, essential oil of Citronella, essential oil of Clary Sage, essential oil of Clove, essential oil of Coriander Seed, essential oil of Cornmint, essential oil of Copaiba Balsam, essential oil of Cypress, essential oil of Davana, essential oil of Elemi, essential oil of Eucalyptus, essential oil of Everlasting (Helichrysum), essential oil of Fennel, essential oil of Fir Needle, essential oil of Frankincense, essential oil of Galbanum, essential oil of Geranium, essential oil of Geranium Rose, essential oil of essential oil of Ginger, essential oil of Grapefruit, essential oil of Hop, essential oil of Hyssop, essential oil of Inula, essential oil of Jasmine, essential oil of Juniper Berry, essential oil of Lavender, essential oil of Lemon, essential oil of Lemon Myrtle, essential oil of Lemon Tea Tree, essential oil of Lemon Verbena, essential oil of Lemongrass, essential oil of Lime, essential oil of Litsea Cubeba, essential oil of Lovage, essential oil of Marjoram, essential oil of Mandarin, essential oil of Melissa, essential oil of Myrrh, essential oil of Neroli, essential oil of Niaouli, essential oil of Nutmeg, essential oil of Orange, essential oil of Oregano, essential oil of Palamarosa, essential oil of Palo Santo, essential oil of Patchouli, essential oil of Peppermint, essential oil of Peru, essential oil of Balsam, essential oil of Petitgrain, essential oil of Pine Needle, essential oil of Plai, essential oil of Ravensara, essential oil of Ravintsara, essential oil of Rosalina, essential oil of Rose, essential oil of Rosehip, essential oil of Rosemary, essential oil of Rosewood, essential oil of Sage, essential oil of Sandalwood, essential oil of Sea Buckthorn, essential oil of Spearmint, essential oil of Spike Lavender, essential oil of Spikenard, essential oil of Spruce, essential oil of Tagetes, essential oil of Tangerine, essential oil of Tea Tree, essential oil of Thyme, essential oil of Tuberose, essential oil of Turmeric, essential oil of Valerian Root, essential oil of Vanilla, essential oil of Vetiver, essential oil of Wintergreen, essential oil of Yarrow, and essential oil of Ylang Ylang.

6. The composition of claim 1, wherein
   the one or more malodor-controlling compositions comprises a blend of essential oils comprising clove oil, bay laurel oil, lemon oil, melissa oil, coriander oil, eucalyptus oil, cinnamon bark oil, citronella oil, palamarosa oil, and clary sage oil.

7. An article of manufacture for the control of malodor and moisture, comprising
   an encasement, the encasement having at least one compartment, and at least one surface which is gas-permeable, and wherein the at least one compartment contains a malodor and moisture control composition, the malodor and moisture control composition comprising smectite clay, a diluent, and at least one malodor-controlling composition.

8. The article of manufacture of claim 7, wherein
   the encasement is made of fabric.

9. The article of manufacture of claim 7, further comprising
   one or more fragrance compositions dissolved within a fixative substance.

10. The article of manufacture of claim 9, wherein
    the fixative substance is selected from the group consisting of polypropylene glycol, polyethylene glycol, and ethylene vinyl acetate copolymer.

11. The article of manufacture of claim 7, wherein
    the one or more fragrance compositions dissolved within a fixative substance is contained in a separate compartment from the malodor and moisture control composition.

12. The article of manufacture of claim 7, further comprising
    a malodor-absorbing component.

13. The article of manufacture of claim 12, wherein
    the malodor absorbing component is activated carbon.

14. The article of manufacture of claim 12, wherein
    the malodor-absorbing component is contained in a separate compartment from the mixture comprising the malodor and moisture control composition.

15. The article of manufacture of claim 7, comprising
    two separate encasements, each comprising one or more compartment, the one or more compartments containing the malodor and moisture control composition.

* * * * *